(12) United States Patent
Tomiyama et al.

(10) Patent No.: US 8,870,801 B2
(45) Date of Patent: Oct. 28, 2014

(54) LOWER LIMB JOINT ORTHOSIS AND CONTROL METHOD THEREFOR

(75) Inventors: Hiroki Tomiyama, Okayama (JP); Tomio Kubo, Hyogo (JP)

(73) Assignee: Hashimoto Artificial Limb Manufacture Corporation, Okayama (JP)

( * ) Notice: Subject to any disclaimer, the term of this patent is extended or adjusted under 35 U.S.C. 154(b) by 179 days.

(21) Appl. No.: 13/390,542

(22) PCT Filed: Sep. 22, 2010

(86) PCT No.: PCT/JP2010/005746
§ 371 (c)(1),
(2), (4) Date: Feb. 15, 2012

(87) PCT Pub. No.: WO2011/036877
PCT Pub. Date: Mar. 31, 2011

(65) Prior Publication Data
US 2012/0143112 A1    Jun. 7, 2012

(30) Foreign Application Priority Data

Sep. 25, 2009  (JP) ................................. 2009-220326

(51) Int. Cl.
*A61F 5/00* (2006.01)
*A61F 2/72* (2006.01)
(52) U.S. Cl.
USPC ............................................. 602/27; 623/27
(58) Field of Classification Search
USPC ............... 602/23–27; 601/5, 33–35; 128/882; 5/621, 624; 623/24–27, 44, 46
See application file for complete search history.

(56) References Cited

U.S. PATENT DOCUMENTS

| | | | |
|---|---|---|---|
| 6,171,272 B1 * | 1/2001 | Akita et al. | 602/28 |
| 6,423,098 B1 * | 7/2002 | Biedermann | 623/24 |
| 6,613,097 B1 * | 9/2003 | Cooper | 623/44 |

FOREIGN PATENT DOCUMENTS

| | | |
|---|---|---|
| JP | 110503929 | 4/1999 |
| JP | 2001-511052 | 8/2001 |
| JP | 2001-299790 | 10/2001 |
| JP | 2004-257568 | 9/2004 |
| JP | 2006-087559 | 4/2006 |
| JP | 2007-524483 | 8/2007 |
| JP | 2008-532704 | 8/2008 |
| WO | 2007/137657 | 6/2007 |

* cited by examiner

*Primary Examiner* — Ophelia A Hawthorne
(74) *Attorney, Agent, or Firm* — Lucas & Mercanti, LLP

(57) ABSTRACT

A lower-limb joint orthosis includes a lower component supporting the foot region, an upper component attached to the lower-limb, and an orthotic joint coupling both components. The orthotic joint includes: a stator including some fluid chambers in which an MR fluid is enclosed; and a rotor including partition plates protruding into the respective fluid chambers. The stator includes a communication path between the anterior chamber and the posterior chamber. The rotor includes connection paths that connect the anterior chambers together, and connect the posterior chambers together. An electromagnet is placed on a side surface of the communication path so that a rotational resistance of the lower component and the upper component is adjusted by adjusting a magnetic force to control the viscosity of the MR fluid that flows through the communication path.

5 Claims, 12 Drawing Sheets

US 8,870,801 B2

LOWER LIMB JOINT ORTHOSIS AND CONTROL METHOD THEREFOR

CROSS-REFERENCE TO RELATED APPLICATION

This Application is a 371 of PCT/JP2010/005746 filed on Sep. 22, 2010 which, in turn, claimed the priority of Japanese Patent Application No. 2009-220326 filed on Sep. 25, 2009, both applications are incorporated by reference herein.

BACKGROUND OF THE INVENTION

1. Field of the Invention

The present invention relates to a lower-limb joint orthosis suitable for use by a paralyzed person whose lower-limb, particularly foot region, is paralyzed, and also relates to a control method therefor.

2. Description of the Related Art

The forms of paralysis of the foot region include: hemiplegia in which mainly one foot is paralyzed due, for example, to apoplexy; and paraplegia in which, in many cases, both feet are paralyzed due, for example, to a spinal cord injury. In either case, it is often difficult or impossible to walk independently. Accordingly, when a person with such a paralysis walks, they need some aid. A conventional aid of this type fixes from the lower leg to the foot by a splint-like object.

This makes it possible to stabilize an upright position, or prevent the person from, for example, stumbling due to the lowering of the toe when separating the foot region from the ground to take a step. A joint function, however, is not provided, and therefore, it is not possible to bend and stretch the ankle in accordance with the shift of the center of the body weight, or absorb shock when the sole makes contact with the ground. Accordingly, walking with the aid attached places a large burden on the body. This causes a paralyzed person to avoid walking independently with the aid attached, or walking with minor assistance. Consequently, also the walking function fails to be improved.

It should be noted that Patent Literature 1 (Japanese Laid-Open Patent Publication No. 2001-299790) shows a lower-limb joint orthosis incorporating a hinge mechanism in the portion corresponding to the ankle joint. In this prior example, however, the orthosis for assisting independence is merely provided with a rotational movement function, and the range of rotational movement is limited to a very narrow range, which does not correspond to a wide angle from landing to stepping. Further, although the locking and unlocking of a hinge mechanism is incorporated, the operation of the hinge mechanism requires the operation of a locking member, which is complicated and cumbersome.

In response, the present applicant has proposed, as the following Patent Literature 2 (Japanese Laid-Open Patent Publication No. 2006-087559), a technique of: providing, in the portion corresponding to the ankle joint, a rotary cylinder in which an MR fluid whose viscosity changes depending on a magnetic force is enclosed; coupling a rotor and a stator of the rotary cylinder to an upper component to be attached to the lower-limb, and to a lower component that supports the foot region; adjusting the viscosity of the MR fluid by adjusting the magnetic force in accordance with the shift of the body weight borne by the sole during walking; and switching the bending and stretching of the ankle (the upward and downward rotational movement of the foot region relative to the ankle) from a disabled or semi-disabled state (referred to as a "locked state") to a freely moving state (referred to as a "free state"). This technique, however, tends to complicate the structure of the lower-limb joint orthosis, and increase the size of the lower-limb joint orthosis.

SUMMARY OF THE INVENTION

It is an object of the present invention to, by further improving the invention of Patent Literature 2 described above, make the structure compact by simplifying it, and also enable a sensitive operation and a high output.

To achieve the above object, the present invention provides a lower-limb joint orthosis including a lower component that supports the foot region, an upper component to be attached to the lower-limb, and an orthotic joint that couples the lower component and the upper component together at a position corresponding to the ankle joint so as to be bendable and stretchable in an up-down direction of the body, the orthotic joint including: a stator including a plurality of fluid chambers which have fan shapes formed by partitioning a short cylindrical enclosed space in a circumferential direction and in which an MR fluid whose viscosity changes depending on a magnetic force is enclosed; and a rotor including partition plates protruding from a shaft section into the respective fluid chambers so as to each secure an anterior chamber anterior to, and a posterior chamber posterior to, the partition plate, the shaft section set at a position of the joint and rotatably supported in the stator, wherein the stator includes, away from the fluid chambers, a communication path that allows communication between the anterior chamber and the posterior chamber of a particular one of the fluid chambers, the rotor includes, in the shaft section, connection paths that connect the anterior chambers of the respective fluid chambers together, and connect the posterior chambers of the respective fluid chambers together, and an electromagnet is placed on a side surface of the communication path so that a rotational resistance of the lower component and the upper component is adjusted by adjusting a magnetic force based on power to be supplied to the electromagnet to control the viscosity of the MR fluid that flows through the communication path.

In addition, the present invention provides, as another configuration, a lower-limb joint orthosis including a lower component that supports the foot region, an upper component to be attached to the lower-limb, and an orthotic joint that couples the lower component and the upper component together at a position corresponding to the ankle joint so as to be bendable and stretchable in an up-down direction of the body, the orthotic joint including: a cylinder including a cylinder chamber in which an MR fluid whose viscosity changes depending on a magnetic force is enclosed; and a piston that moves back and forth within the cylinder chamber so as to secure an anterior chamber anterior to, and a posterior chamber posterior to, the piston, wherein one end of the cylinder or the piston is set at a position of the joint, communication paths are provided outside the cylinder chamber, the communication paths allowing communication between the anterior chamber and the posterior chamber of the cylinder chamber, and an electromagnet is placed on side surfaces of the communication paths so that a rotational resistance of the lower component and the upper component is adjusted by adjusting a magnetic force based on power to be supplied to the electromagnet to control the viscosity of the MR fluid that flows through the communication paths.

In addition, the present invention provides, as a control method for the above lower-limb joint orthoses, a control method for a lower-limb joint orthosis, the method controlling a rotational resistance of the rotor and the stator, or a resistance to advancement and retreat of the piston and the cylinder, wherein a sensor that detects load is attached to an underside surface of the lower component so that the resistance is controlled by adjusting, in accordance with an output of the sensor, power to be supplied to the electromagnet.

In the invention, an MR fluid cylinder is a rotary cylinder including a plurality of fluid chambers in which an MR fluid is enclosed. This makes it possible to increase the sensitivities of a locked state and a free state of an orthotic ankle joint that are obtained by changing the viscosity of the MR fluid, increase the output, and reduce the size. Further, the adjustment of the viscosity of the MR fluid is made by the magnetic force of the electromagnet. This simplifies the structure and also facilitates the control. In the invention, an MR cylinder is a reciprocating cylinder. This simplifies the structure. Based on the invention, it is possible to automatically control the rotational resistance of a lower component and an upper component in accordance with the state of the bending and stretching of the ankle in the orientation of the leg during walking. This makes it possible to achieve a motion close to that of the ankle joint of a living body.

DESCRIPTION OF THE EMBODIMENTS

Figure 1:
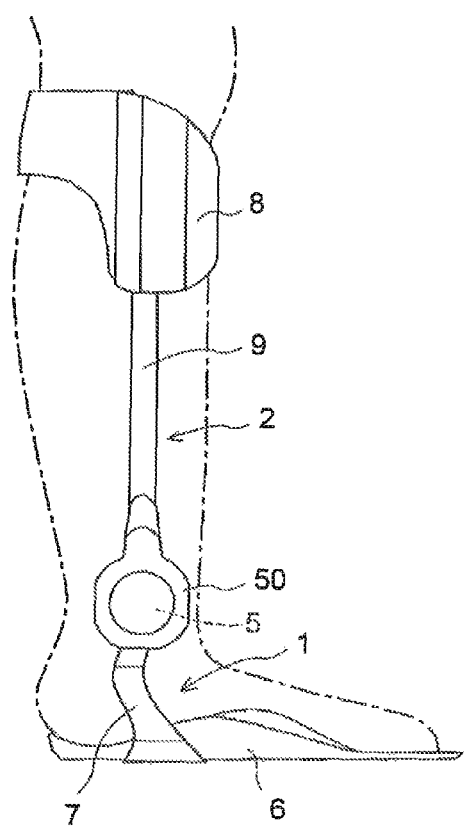
FIG. 1 is a side view of a lower-limb joint orthosis according to a first embodiment.
Figure 2:
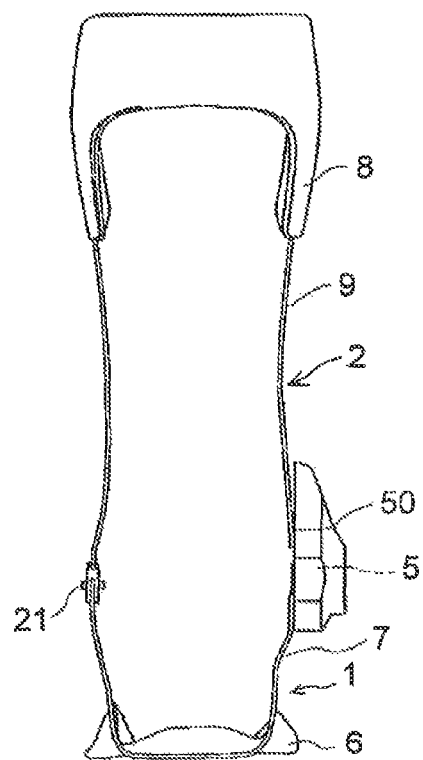
FIG. 2 is a rear view of the lower-limb joint orthosis according to the first embodiment.
Figure 3:
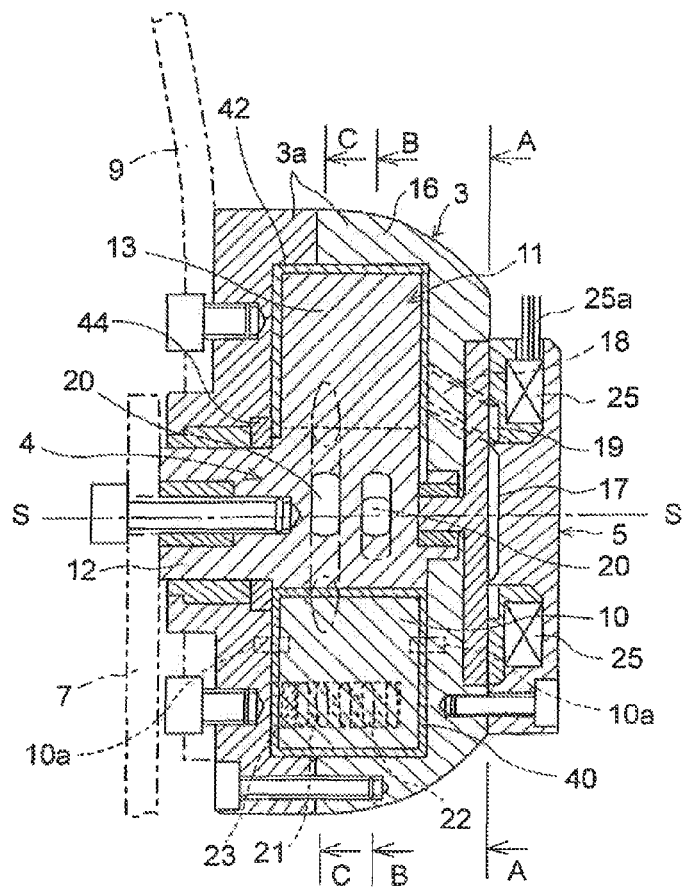
FIG. 3 is a vertical cross-sectional view of an orthotic joint included in the lower-limb joint orthosis according to the first embodiment.
Figure 4:
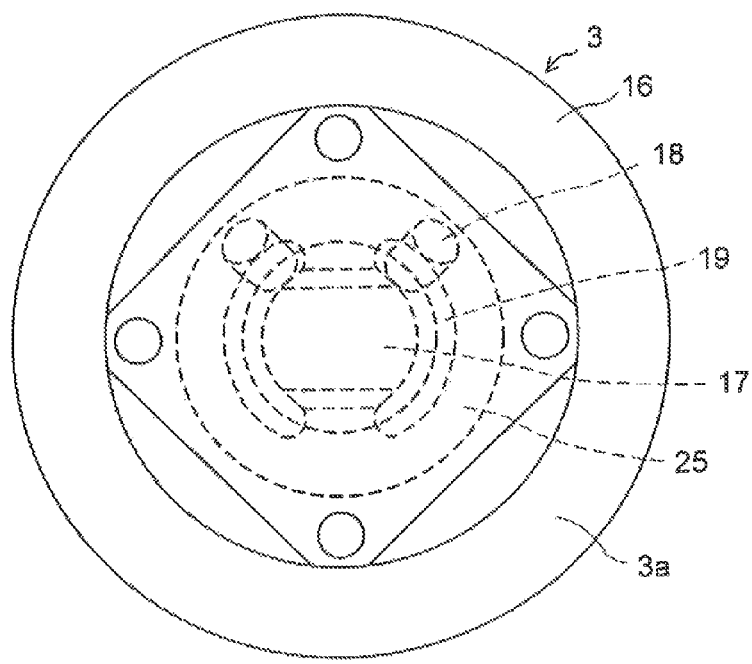
FIG. 4 is a right side view of the orthotic joint included in the lower-limb joint orthosis according to the first embodiment.
Figure 5:
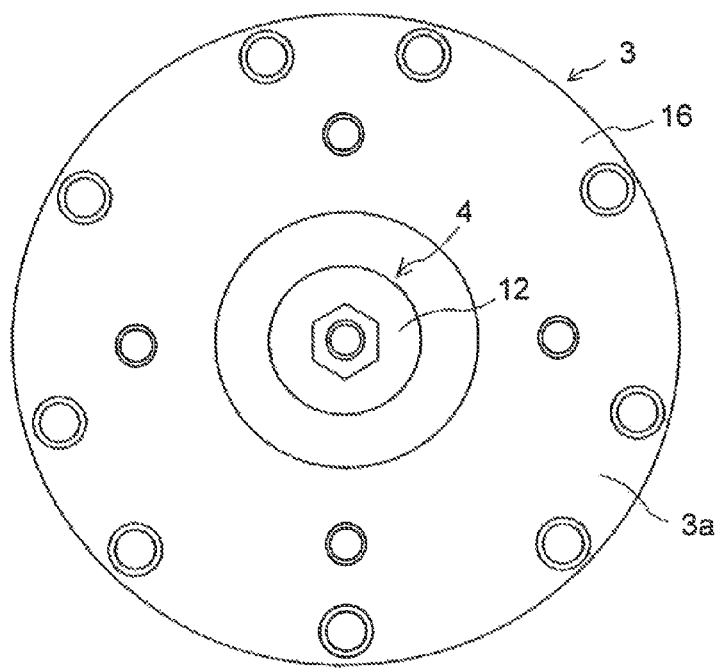
FIG. 5 is a left side view of the orthotic joint included in the lower-limb joint orthosis according to the first embodiment.
Figure 6:
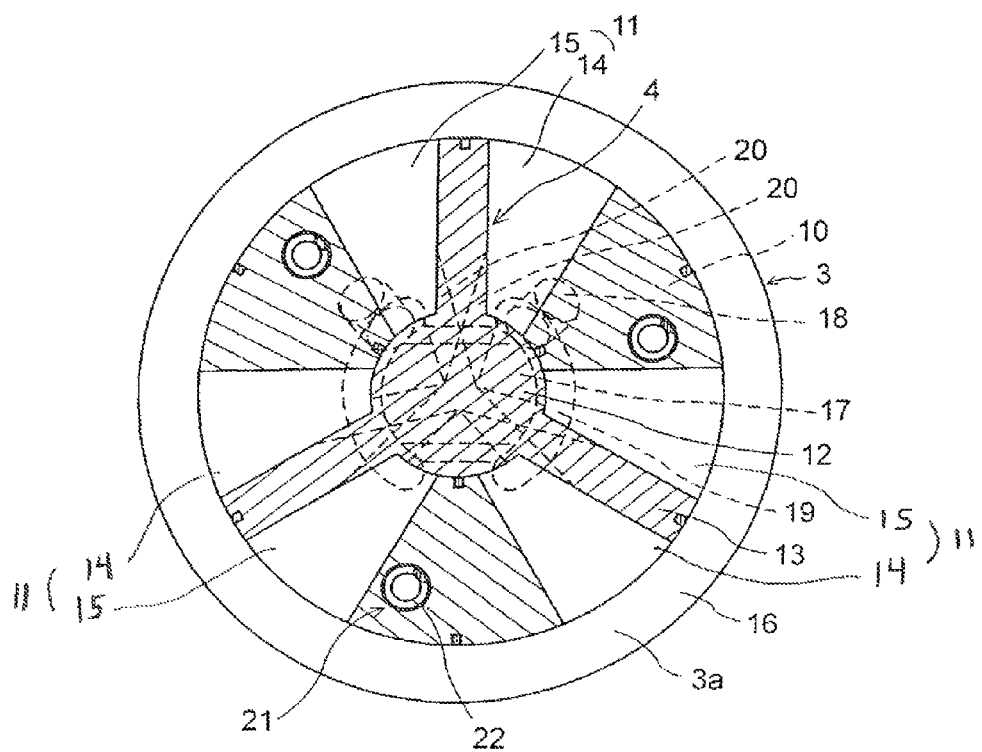
FIG. 6 is a cross-sectional view from a lateral view of the orthotic joint included in the lower-limb joint orthosis according to the first embodiment.

With reference to the drawings, a description is given below of embodiments of the present invention. FIG. 1 is a side view of a lower-limb joint orthosis provided with an ankle-joint function according to a first embodiment of the present invention; FIG. 2 is a rear view thereof; FIG. 3 is a vertical cross-sectional view of an orthotic joint included in the lower-limb joint orthosis; FIG. 4 is a right side view thereof; FIG. 5 is a left side view thereof; and FIG. 6 is a horizontal cross-sectional view thereof.

In the lower-limb joint orthosis (hereinafter also referred to simply as an "orthosis") according to the present embodiment, an MR fluid cylinder is a rotary cylinder. The lower-limb joint orthosis includes a lower component 1, an upper component 2, and an orthotic joint 5 that couples the lower component 1 and the upper component 2 together. The lower component 1 is capable of supporting the sole mounted thereon; the upper component 2 is to be attached to the lower-limb; and the orthotic joint 5 includes a stator 3 and a rotor 4. It should be noted that FIGS. 1 and 2 show the state where a cover 50 is attached to the surface of the orthotic joint 5.

The lower component 1 includes a shoe-like foot-mounting section 6, and a lower strut 7 extending upward from the right and left (in attachment) of the foot-mounting section 6. The upper component 2 includes an attachment body 8 capable of being attached to the lower-limb, and an upper strut 9 extending downward from the right and left (in attachment) of the attachment body 8. The attachment of the orthosis is performed in the manner of wearing a boot. That is, the foot is inserted into the foot-mounting section 6 (while the instep is held by a band or the like), and the attachment body 8 is attached to the lower leg. It should be noted that in the case of a hemiplegic person, the orthosis according to the present invention is attached to the paralyzed lower-limb. In the case of a paraplegic person, the orthosis is attached to the lower limb on each side.

The stator 3 is fixed to the upper strut 9, and includes three fluid chambers 11 having fan shapes formed by partitioning a short cylindrical enclosed space, surrounded by a casing 3a, in the circumferential direction by three weirs 10. In the fluid chambers 11, an MR fluid described later is enclosed. It should be noted that the weirs 10 are fixed within the casing 3a by knock pins 10a. At the surfaces of the weirs 10 that are in contact with the casing 3a, packings 40 formed of a fluororesin or the like are attached to the entire circumferences of the weirs 10 in order to maintain liquid tightness.

It should be noted that in the present embodiment, the case is shown where the three fluid chambers 11 are provided within the stator 3. Alternatively, the number of fluid chambers 11 provided within the stator 3 may be two, or may be four or more.

The rotor 4 is fixed to the lower strut 7 (the attachments of the stator 3 and the rotor 4 to the respective components may be switched). The rotor 4 includes a shaft section 12 rotatably inserted in the center of the stator 3, and partition plates 13 protruding radially from the shaft section 12 into the respective fluid chambers 11. Accordingly, the partition plates 13 partition the respective fluid chambers 11 into anterior chambers 14 and posterior chambers 15. With such a configuration, even if an attempt is made to cause the shaft section 12 to rotate, the MR fluid filling the anterior chambers 14 and the posterior chambers 15 cannot escape, and therefore, the shaft section 12 does not rotate. It should be noted that at the surfaces of the partition plates 13 that slide against the casing 3a of the stator 3, packings 42 formed of a fluororesin or the like are also attached to the partition plates 13 of the rotor 4 in order to maintain liquid tightness. Further, the numeral 44 in FIG. 3 represents a magnetic seal wrapped around the entire circumference of the shaft section 12.

Figure 7:
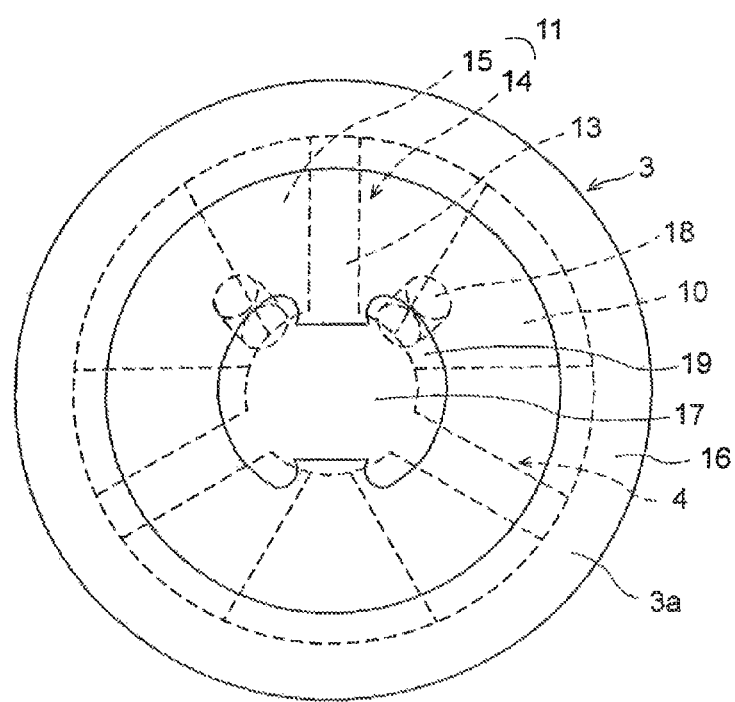
FIG. 7 is a cross-sectional view along line A-A of FIG. 3.
Figure 8:
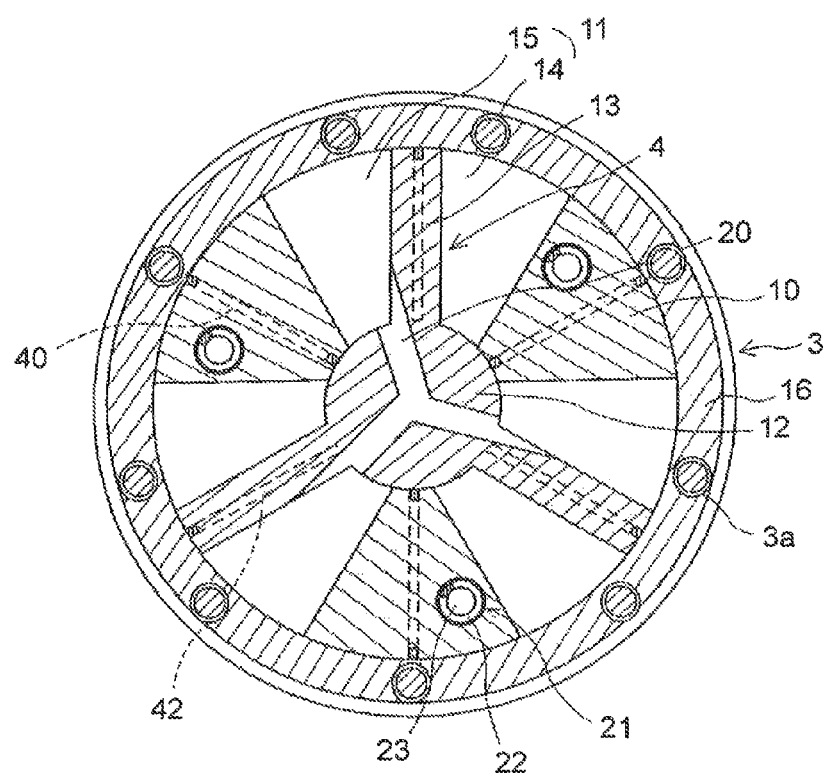
FIG. 8 is a cross-sectional view along line B-B of FIG. 3.
Figure 9:
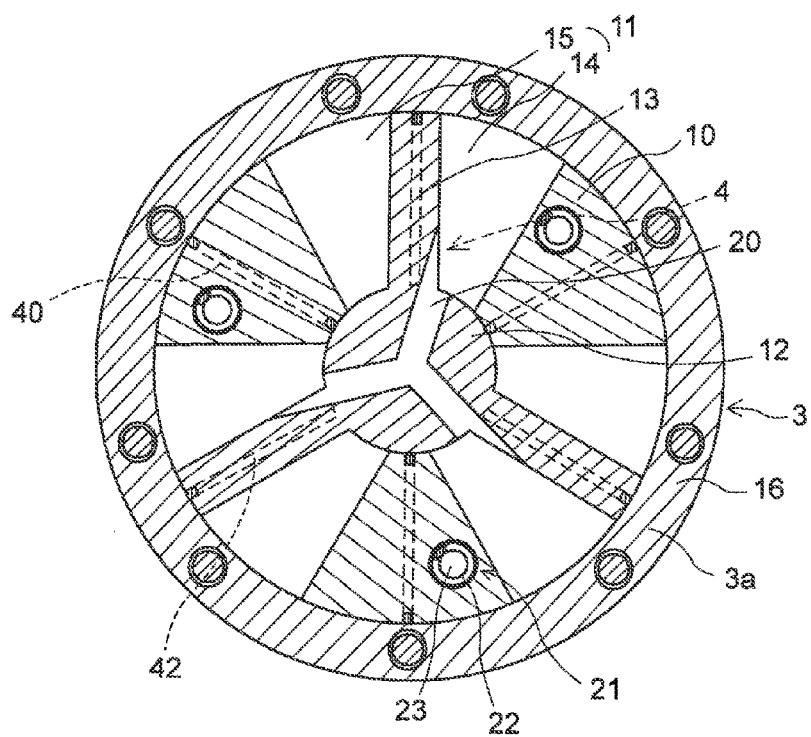
FIG. 9 is a cross-sectional view along line C-C of FIG. 3.

As described above, the MR fluid filling the anterior chambers 14 and the posterior chambers 15 cannot escape in this state, and therefore, the rotor 4 cannot rotate. In response, at a position separated from the fluid chambers 11 by a chamber wall 16 of the stator 3, a communication path 17 is provided that allows communication between the anterior chamber 14 and the posterior chamber 15 of a particular one of the fluid chambers 11. FIG. 7 is a cross-sectional view along line A-A of FIG. 3; FIG. 8 is a cross-sectional view along line B-B; and FIG. 9 is a cross-sectional view along line C-C. The communication path 17 according to the present embodiment is defined as follows. Two independent arcuate paths 19 are provided that are connected to the anterior chamber 14 and the posterior chamber 15 of the fluid chamber 11 via guide paths 18, and a band-like zone formed between the arcuate paths 19 is the communication path 17. In this case, the width of the communication path 17 is set to be shorter than the arc length of each arcuate path 19.

The formation of the communication path 17 for the anterior chamber 14 and the posterior chamber 15 of each fluid chamber 11 allows the MR fluid in the anterior chamber 14 and the posterior chamber 15 to flow between the posterior chamber 15 and the anterior chamber 14. This enables the rotation of the partition plates 13, that is, the shaft section 12. If, however, the communication path 1 is provided for each fluid chamber 11, such a configuration is complicated, and also has a space problem. Accordingly, in the present embodiment, the shaft section 12 of the rotor 4 includes connection paths 20 that connect the anterior chambers 14 of the respective fluid chambers 11 together, and connect the posterior chambers 5 of the respective fluid chambers 11 together. It should be noted that the connection paths 20 are provided in two tiers in the axial direction of the shaft section 12 so as to be separated from each other for the anterior chambers 14 and for the posterior chambers 15.

Consequently, to cause the rotor 4 to advance (rotate clockwise in FIG. 6), the MR fluid in the anterior chamber 14 of the particular fluid chamber 11 flows into the posterior chamber 14 through the guide paths 18, the arcuate paths 19, and the communication path 17. Also the MR fluid in the anterior chambers 14 of the other fluid chambers 11 flows into the posterior chambers 15 through the connection path 20, and ultimately flows into the posterior chamber 15 of the particular fluid chamber 11. This enables the rotation of the shaft section 12, that is, the rotor 4. On the other hand, to cause the rotor 4 to retreat, the MR fluid follows the route opposite to that described above.

It should be noted that the expansion of the MR fluid due, for example, to temperature changes may increase the internal pressures of the fluid chambers 11. This may cause the MR fluid to leak out of the fluid chambers 11. In response, in the present embodiment, a buffer chamber 21 is provided through an opening formed on a side surface of each weir 10. Then, in the buffer chamber 21, a spring 22 is placed that has a spring modulus stronger than the internal pressure of each fluid chamber 11 in operation. Also, on the opening side of the buffer chamber 21, an adjustment plate 23 is provided that is triggered by the spring 22 and slides within the buffer chamber 21. This causes the MR fluid to flow into the buffer chamber 21 when the internal pressure of the fluid chamber 11 has excessively increased, and thereby prevents the MR fluid from leaking out of the fluid chamber 11.

Incidentally, the capabilities of the stator 3 and the rotor 4 to rotate relative to each other mean the capabilities of the lower component 1 and the upper component 2 to rotate (the capability of the ankle to bend and stretch). The rotational resistance at this time (the resistance to the bending and stretching of the ankle), however, varies depending on the magnetic force applied to the MR fluid. When and to what degree the rotational resistance is set during walking will be described later. In this case, the orthotic joint 5 is incorporated in the portions of the lower strut 7 and the upper strut 9 that are located outside the lower-limb, and at this time, the shaft section 12 of the rotor 4 is set at the position of the ankle joint. Meanwhile, the portions of the lower strut 7 and the upper strut 9 that are located inside the lower-limb also need to be rotatable, and therefore are pivotally attached together by a pin 24 concentric with the shaft section 12.

The placement of an electromagnet 25 (the numeral 25a represents a power line) on a side surface of the communication path 17 so as to surround it makes it possible to control the rotational resistance of the lower component 1 and the upper component 2 by adjusting the power to be supplied to the electromagnet 25 to change the viscosity of the MR fluid that flows through the communication path 17. To this end, the communication path 17 is brought close to the electromagnet 25; the surface of the communication path 17 that opposes the electromagnet 25 is made wide; and the communication path 17 is shaped into a shallow groove. This enables a sensitive response to the magnetic force applied by the electromagnet 25. Additionally, the electromagnet 25 is a circular magnet formed along the shape of the communication path 17.

It should be noted that, to fulfill the functions as described above, the members adjacent to the MR fluid, namely the stator 3 and the rotor 4, are preferably formed of a non-magnetic material such as aluminum. Alternatively, instead of the formation of the entireties of the stator 3 and the rotor 4 with a non-magnetic material such as aluminum, only the portions of the stator 3 and the rotor 4 that make contact with the MR fluid may be formed of a non-magnetic metallic material such as aluminum, and the portions that do not make contact with the MR fluid and do not require a high abrasion resistance may be formed of a synthetic resin such as a thermoplastic resin. Such hybridization of a non-magnetic metallic material and a synthetic resin makes it possible to economically mass-produce the orthotic joint 5, and also achieve a further reduction in weight of the orthotic joint 5. Further, on the surfaces of the stator 3 and the rotor 4 that make contact with the MR fluid, an abrasion-resistant coating layer formed of a DLC (Diamond-like Carbon) or the like may be provided.

Incidentally, the MR fluid (Magnetorheological fluid) described above is a magnetizable fluid obtained by mixing a viscous fluid with a magnetic powder, and has the following properties. When magnetism is applied to the MR fluid, the MR fluid congeals, and does not flow by fulfilling a solid-like function. When the application of magnetism is stopped, the congelation is ceased, and the MR fluid flows freely. In other words, the MR fluid refers to a fluid whose viscosity changes depending on the magnetic force applied thereto. As such an MR fluid, those manufactured by LORD Corporation are well known and commercially available under product names MRF-132AD and MRF-122-2ED.

Next, a description is given of the motion of the orthotic joint 5 when a paralyzed person wearing the above orthosis 1 walks. The ankle of a living body varies in the degree of bending and stretching depending on the orientation of the leg, and therefore, the orthotic joint 5 makes the same motion as that of the ankle. That is, after the foot region has stepped and the underside surface of the foot-mounting section 4 of the lower component 2 has made contact with the ground (a midstance), the upper component 3 sequentially leans forward toward the lower component 2 in accordance with the shift of the body weight. That is, the rotation of the orthotic joint 5 needs to be free to some extent during the time from the midstance to a terminal stance. On the other hand, when the foot-mounting section 4 has separated from the ground by lifting the same foot region (a swing phase), it is preferable to maintain an acute angle state (dorsiflexion), which corresponds to the angle of the upper component 3 relative to the lower component 2 at the moment of the separation. That is, the orthotic joint 5 needs to be locked in the swing phase.

This is the case of a severely paralyzed person. If the orthotic joint 5 is not locked, the toe may lower due to the rotation of the orthotic joint 5 by, for example, the weight of the foot, and the person may stumble and fall. In this regard, the following description is given of the state where the rotation of the orthotic joint 5 is locked and the state where the rotation of the orthotic joint 5 is free. The locked state and the free state of the rotation of the orthotic joint 5 can be controlled by the viscosity of the MR fluid that flows through the communication path 17. Accordingly, the control is performed by adjusting the power (voltage or current) to be supplied to the electromagnet 25. When the power to be supplied to the electromagnet 25 is increased, a large magnetic force is applied to the MR fluid, and therefore, the viscosity of the MR fluid increases. Consequently, the rotational resistance of the orthotic joint 5 increases. On the other hand, when the power is reduced, the rotational resistance decreases.

This makes it only necessary to reduce the magnetic force in the stance phase and increase the magnetic force in the swing phase. In practice, however, a wearer of the orthosis cannot perform such an operation themselves. In response, a sensor (not shown) is provided that determines whether or not the foot-mounting section 4 has made contact with the ground. Then, the magnetic force of the electromagnet 25 is adjusted on the basis of the determination. The sensor may be one that detects the angle of rotational movement of the shaft section 12, or detects the height above the ground of the foot-mounting section 4. In the present invention, the sensor is a load meter, which is simple and operates with certainty, and the load meter is attached to the underside surface of the foot-mounting section 4.

The load meter is one that determines whether or not load (the body weight) has been borne by the foot-mounting section 6, and is one capable of obtaining an output (voltage) corresponding to strain or displacement, such as a strain meter or a displacement meter. Then, the output of the load meter is measured, and the power corresponding to the output is defined as the setting condition of the power to be supplied to the electromagnet 25. Accordingly, in the stance phase, the output from the load meter varies, and a small power is supplied to the electromagnet 25. Consequently, the magnetic force decreases, and the viscosity of the MR fluid decreases. This enables the lower component 1 to relatively freely rotate relative to the upper component 2 (enables the ankle to bend and stretch). On the other hand, in the swing phase, the situation is the opposite to the above (the bending and stretching of the ankle is limited). The angle of the ankle at this time, however, can maintain the orientation obtained at the moment when the foot-mounting section 6 has separated from the ground. This enables even a paralyzed person to walk smoothly.

In this case, it is also possible to provide numerous sensors on the underside surface of the foot-mounting section 6 in an appropriate distribution, and determine which sensor has responded. Consequently, the output from each sensor sequentially varies in each process of the stance. This makes it also possible to produce magnetic forces different depending on the process, and therefore generate a motion closer to the ankle of a living body.

The above is the case where the rotation of the orthotic joint 5 is made completely free in the stance phase. However, in the case of a more severe paralysis, or, conversely, in the case of a mild paralysis, or in the case of convalescence, there is a case where it is preferable to allow the rotation of the orthotic joint 5 with some resistance even in the stance phase. For example, in the case of a severely paralyzed person having difficulty in standing independently in the stance phase, if the orthotic joint 5 is capable of rotating completely freely, the person may fall. Conversely, in the case of a mild paralysis or convalescence, the provision of resistance to the rotation of the orthotic joint 5 in the step phase can facilitate the taking off of the paralyzed side.

This is also true of the swing phase. There is a case where it is preferable to require some force to maintain the orthotic joint 5 in dorsiflexion without completely locking the rotation of the orthotic joint 5 even in the swing phase. Specifically, if this is applied to a convalescent paralyzed person or the like, this serves as training in exerting a force to lock the rotation, which enhances the walking function. In any of the above cases, the power to be supplied to the electromagnet 25 may be moderated on the basis of the output from the sensor. It should be noted that in the rotary cylinder according to the present embodiment, the three fluid chambers 11 are formed so that the partition plates 13, that is, the rotor 4, can rotate by up to 60°. This is because the angle of bending and stretching of the ankle joint of a living body is 60°, and also because it is possible to form numerous cylinder chambers 11, and therefore increase the range of the control of the rotational resistance.

Figure 10:
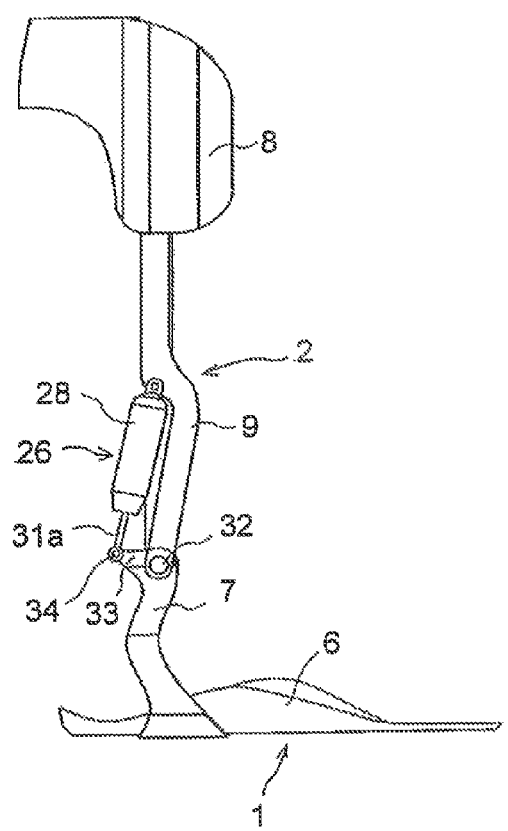
FIG. 10 is a side view of a lower-limb joint orthosis according to a second embodiment.
Figure 11:
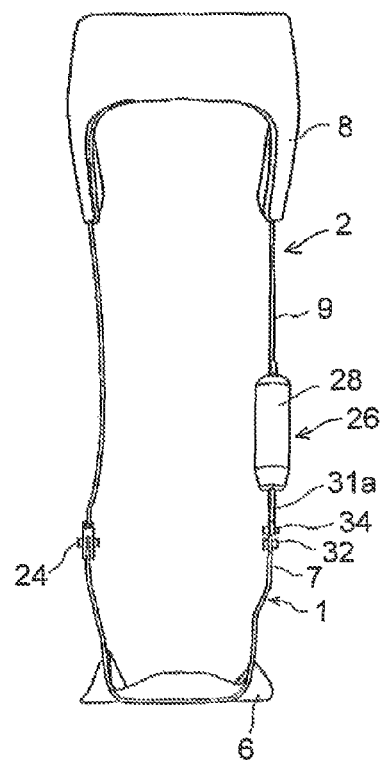
FIG. 11 is a rear view of the lower-limb joint orthosis according to the second embodiment.
Figure 12:
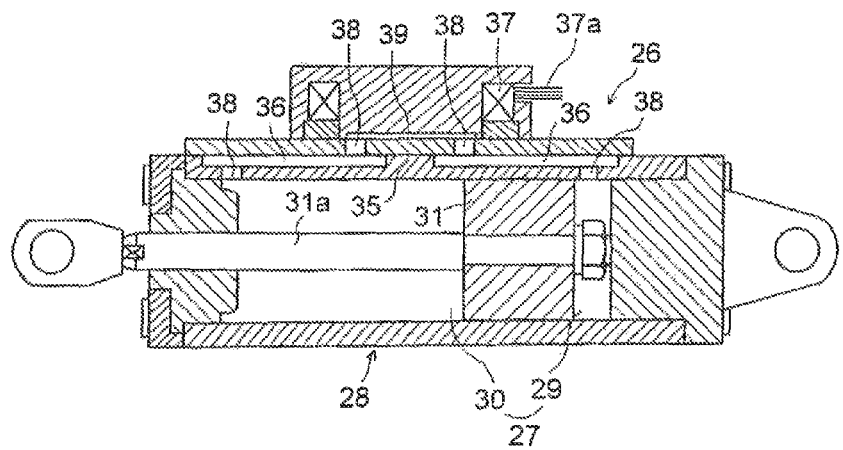
FIG. 12 is a cross-sectional view of an orthotic joint included in the lower-limb joint orthosis according to the second embodiment.
Figure 13:
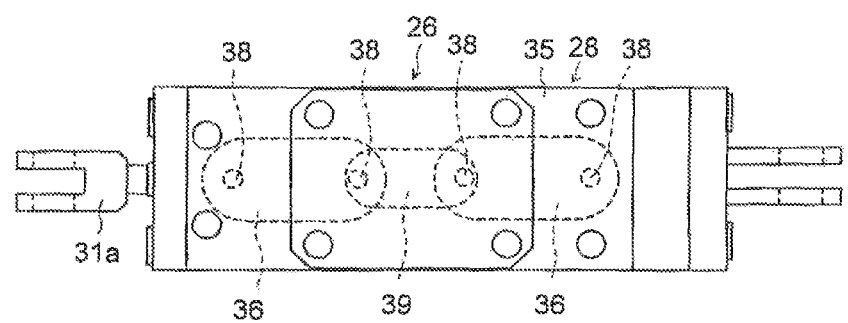
FIG. 13 is a side view of the orthotic joint included in the lower-limb joint orthosis according to the second embodiment.

FIG. 10 is a side view of an orthosis likewise provided with an ankle-joint function according to a second embodiment; FIG. 11 is a rear view thereof; FIG. 12 is a cross-sectional view of an orthotic ankle joint included in the orthosis; and FIG. 13 is a side view thereof in the present embodiment, an MR fluid cylinder included in an orthotic, joint 26 is a reciprocating cylinder. Specifically, the orthotic joint 26 includes: a cylinder 28 having a cylinder chamber 27 in which an MR fluid is enclosed; and a piston 31 that moves hack and forth within the cylinder chamber 27 so as to secure an anterior chamber 29 anterior to, and a posterior chamber 30 posterior to, the piston 31. One end of a piston rod 31a protruding from the cylinder 28 is pivotally attached by a coupling pin 34 to an arm 33 fixed to a coupling shaft 32 that pivotally attaches a lower component 1 and an upper component 2 together, while the other end of the cylinder 28 is coupled to the upper component 2. It should be noted that these attachments to the respective components can be switched in a similar manner to the case of the first embodiment, and the portions of the lower component 1 and the upper component 2 that are located inside are pivotally attached together by a pin 24 concentric with the coupling shaft 32 also in a similar manner to the case of the first embodiment.

In the anterior chamber 29 and the posterior chamber 30 of the cylinder chamber 27, the MR fluid is likewise enclosed. On a chamber wall 35 of the cylinder 28, communication paths 36 are formed that connect the anterior chamber 29 and the posterior chamber 30 together. On side surfaces of the communication paths 36, an electromagnet 37 (the numeral 37a represents a power line) is placed. The communication paths 36 according to the present embodiment communicate with each other via communication holes 38 through a bridging path 39 provided in the middle between the communication paths 36. To enable a sensitive response to the magnetic force applied by the electromagnet 37, the bridging path 39 is brought close to the electromagnet 37, the surface of the bridging path 39 that opposes the electromagnet 37 is made wide; and the bridging path 39 is shaped into a shallow groove. Further, the electromagnet 37 is a rectangular magnet surrounding the bridging path 39.

This makes it possible to change the viscosity of the MR fluid by adjusting the power to be supplied to the electromagnet 37, and therefore adjust the resistance to the advancement and retreat of the piston 31, that is, the rotational resistance of the lower component 1 and the upper component 2. It should be noted that the attachment of a sensor to the underside surface of the lower component 1, the control performed for the adjustment, and the like are the same as those of the case of the first embodiment described above. In the orthosis according to the present embodiment, the MR fluid cylinder can be a regular reciprocating cylinder. This provides the advantage that the structure is simplified. Further, the provision of two coupling points makes it possible, by devising the coupling structure, to cause the lower leg and the foot to move rotationally to some extent.

The above lower-limb joint orthoses are each provided with a joint function for the ankle joint. Alternatively, each orthosis may be provided with a joint function for the knee joint. In this case, the lower component 1 extends to near the knee without providing the ankle-joint function, and the upper component 2 is attached to the upper leg (the shaft section 12 is set at the knee joint). The rotational resistance of the MR fluid cylinder, however, is controlled by the sensor in each of the swing phase, the stance phase, and the step phase in a similar manner to the above lower-limb joint orthoses. Yet alternatively, each orthosis may be provided with both the ankle-joint function and the knee-joint function. Although the control is complicated, the output from the sensor may be output to the MR fluid cylinder by a program. Yet alternatively, each orthosis may be attached to the upper limb. Specifically, each orthosis is provided with an elbow-joint function or a wrist-joint function. In this case, generally, the control is performed manually.

What is claimed is:

1. A lower-limb joint orthosis including a lower component that supports the foot region, an upper component configured to be attached to the lower-limb, and an orthotic joint that couples the lower component and the upper component together at a position corresponding to the ankle joint so as to be bendable and stretchable in an up-down direction of the body, the orthotic joint comprising:
    a stator including a plurality of fluid chambers which have fan shapes formed by partitioning a short cylindrical enclosed space in a circumferential direction and in which an MR fluid whose viscosity changes depending on a magnetic force is enclosed; and
    a rotor including partition plates protruding from a shaft section into the respective fluid chambers so as to each secure an anterior chamber anterior to, and a posterior chamber posterior to, the partition plate, the shaft section set at a position of the orthotic joint and rotatably supported in the stator, wherein
    the stator includes a communication path positioned away from the fluid chambers, that allows communication between the anterior chamber and the posterior chamber of a particular one of the fluid chambers, the rotor includes, in the shaft section, connection paths that connect the anterior chambers of the respective fluid chambers together, and connect the posterior chambers of the respective fluid chambers together, and
    an electromagnet is placed on a side surface of the communication path so that a rotational resistance of the lower component and the upper component is adjusted by adjusting a magnetic force based on power to be supplied to the electromagnet to control the viscosity of the MR fluid that flows through the communication path.

2. The lower-limb joint orthosis according to claim 1, wherein
    the communication path is a band-shaped path formed between two semi-circular paths connected to the anterior chamber and the posterior chamber of the particular fluid chamber via guide paths, the band-shaped path allowing communication between the two semi-circular paths, and
    the electromagnet is a circular magnet surrounding the communication path.

3. The lower-limb joint orthosis according to claim 1, wherein
    the fluid chambers are three divided chambers, and the partition plates rotate in a range of 60° in the respective fluid chambers.

4. A lower-limb joint orthosis including a lower component that supports the foot region, an upper component to be attached to the lower-limb, and an orthotic joint that couples the lower component and the upper component together at a position corresponding to the ankle joint so as to be bendable and stretchable in an up-down direction of the body,
    the orthotic joint comprising:
        a cylinder including a cylinder chamber in which an MR fluid whose viscosity changes depending on a magnetic force is enclosed; and
        a piston that moves back and forth within the cylinder chamber so as to secure an anterior chamber anterior to, and a posterior chamber posterior to, the piston, wherein
    one end of the cylinder or the piston is set at a position of the orthotic joint,
    communication paths are provided outside the cylinder chamber, the communication paths allowing communication between the anterior chamber and the posterior chamber of the cylinder chamber, and
    an electromagnet is placed on side surfaces of the communication paths so that a rotational resistance of the lower component; and the upper component is adjusted by adjusting a magnetic force based on power to be supplied to the electromagnet to control the viscosity of the MR fluid that flows through the communication paths, wherein
    the communication paths are formed on a chamber wall of the cylinder so as to communicate with each other through a bridging path provided in a middle between the communication paths, and the electromagnet is a rectangular magnet surrounding the bridging path.

5. A control method for a lower-limb joint orthosis, the method controlling a rotational resistance of the rotor and the stator of, or a resistance to advancement and retreat of the piston and the cylinder of, the joint orthosis according to claim 1, wherein
    a sensor that detects load is attached to an underside surface of the lower component so that the resistance is controlled by adjusting, in accordance with an output of the sensor, power to be supplied to the electromagnet.

* * * * *